(12) United States Patent
Isoda et al.

(10) Patent No.: US 11,391,728 B2
(45) Date of Patent: Jul. 19, 2022

(54) PHOSPHOR-INTEGRATED NANOPARTICLES USED IN FLUORESCENCE OBSERVATION

(71) Applicant: Konica Minolta, Inc., Tokyo (JP)

(72) Inventors: Takeshi Isoda, Sayami (JP); Masaru Takahashi, Kokubunji (JP)

(73) Assignee: KONICA MINOLTA, INC., Tokyo (JP)

( * ) Notice: Subject to any disclaimer, the term of this patent is extended or adjusted under 35 U.S.C. 154(b) by 93 days.

(21) Appl. No.: 15/544,721

(22) PCT Filed: Jan. 21, 2015

(86) PCT No.: PCT/JP2015/051522
§ 371 (c)(1),
(2) Date: Jul. 19, 2017

(87) PCT Pub. No.: WO2016/117054
PCT Pub. Date: Jul. 28, 2016

(65) Prior Publication Data
US 2018/0011086 A1   Jan. 11, 2018

(51) Int. Cl.
*G01N 33/533* (2006.01)
*G01N 33/58* (2006.01)
(Continued)

(52) U.S. Cl.
CPC ............ *G01N 33/533* (2013.01); *C09K 11/02* (2013.01); *G01N 33/48* (2013.01); *G01N 33/53* (2013.01);
(Continued)

(58) Field of Classification Search
CPC ...... G01N 33/533; G01N 33/48; G01N 33/53; G01N 33/582; C09K 11/02; C09K 11/0805; C09K 11/0883; C08K 5/0025
See application file for complete search history.

(56) References Cited

U.S. PATENT DOCUMENTS

| 6,399,397 B1 | 6/2002 | Zarling et al. |
| 2009/0061226 A1* | 3/2009 | Banin ............... C08K 3/22 428/402 |

(Continued)

FOREIGN PATENT DOCUMENTS

| AU | 2005248419 C1 | 12/2005 |
| EP | 2589642 A1 | 5/2013 |

(Continued)

OTHER PUBLICATIONS

Extended European Search Report corresponding to Application No. 15878749.9-1105/3249403 PCT/JP2015051522; dated Dec. 17, 2018.

(Continued)

*Primary Examiner* — Tracy Vivlemore
*Assistant Examiner* — Nam P Nguyen
(74) *Attorney, Agent, or Firm* — Cantor Colburn LLP

(57) ABSTRACT

The present invention may provide phosphor-integrated nanoparticles whose precipitation and/or aggregation, particularly aggregation can be inhibited upon carrying out immunostaining therewith and which can thus be used for staining even after long-term storage without requiring a complicated operation, the phosphor-integrated nanoparticles preferably maintaining excellent performance, such as staining properties, even after long-term storage. The phosphor-integrated nanoparticles of the present invention have an average sphericity (f) of 0.80 to 0.95 and preferably have an average circumference ratio (R) of 0.50 to 0.95. More preferably, the matrix of the particles contains an organic compound, the phosphor-integrated nanoparticles have an average particle size of 300 nm or less, and a biological component-binding molecule is bound on the particle

11 Claims, 1 Drawing Sheet

(Example 1)

(Comparative Example 1)

(51) Int. Cl.
   G01N 33/48   (2006.01)
   G01N 33/53   (2006.01)
   C09K 11/02   (2006.01)
   C08K 5/00   (2006.01)
   C09K 11/08   (2006.01)

(52) U.S. Cl.
   CPC ......... G01N 33/582 (2013.01); *C08K 5/0025* (2013.01); *C09K 11/0805* (2013.01); *C09K 11/0883* (2013.01)

(56) References Cited

U.S. PATENT DOCUMENTS

| | | | |
|---|---|---|---|
| 2011/0020241 A1 | 1/2011 | Tsukada et al. | |
| 2012/0142808 A1* | 6/2012 | Izu | B82Y 30/00 522/111 |
| 2012/0168671 A1* | 7/2012 | Wang | C09K 11/06 252/62.56 |
| 2012/0323112 A1* | 12/2012 | Jokerst | A61B 8/481 600/420 |
| 2014/0004049 A1* | 1/2014 | Rao | A61K 49/0054 424/9.6 |
| 2015/0079611 A1* | 3/2015 | Takanashi | G01N 33/582 435/7.23 |

FOREIGN PATENT DOCUMENTS

| | | | | |
|---|---|---|---|---|
| JP | H10212223 A | | 8/1998 | |
| JP | 2002194347 A | | 7/2002 | |
| JP | 2008543982 A | | 12/2008 | |
| JP | 2010048932 A | | 3/2010 | |
| JP | 2014-163758 A1 | * | 9/2014 | ........... G01N 33/533 |
| JP | 2014163758 A | * | 9/2014 | |
| JP | 2014163758 A | | 9/2014 | |
| JP | 6614161 B2 | | 12/2019 | |
| WO | WO-2013147081 A1 | * | 10/2013 | |
| WO | 2014203614 A1 | | 12/2014 | |

OTHER PUBLICATIONS

JPO Notification of Reason for Rejection corresponding to JP Application No. 2016-570400; dated Sep. 11, 2018.
International Search Report corresponding to Application No. PCT/JP2015/051522; dated Apr. 7, 2015.
Written Opinion of the International Searching Authority corresponding to Application No. PCT/JP2015/051522; dated Apr. 7, 2015.
JPO Decision of Refusal corresponding to Application No. 2016-570400; dated Apr. 23, 2019.
Extended European Search Report corresponding to Application No. 15878749.9; dated Dec. 16, 2019.
EPO Office Action for corresponding EP Application No. 15878749.9; dated Oct. 21, 2020.
JPO Notification of Reasons for Refusal for corresponding JP Application No. 2019-134465, dated Sep. 8, 2020.
JPO Notice of Reasons for Refusal for corresponding JP Application No. 2019-134465; dated Apr. 20, 2021.

* cited by examiner (Example 1)               (Comparative Example 1)
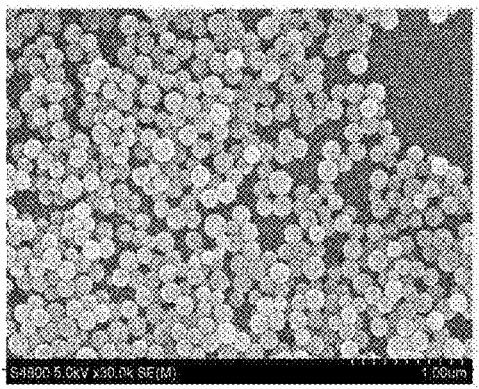 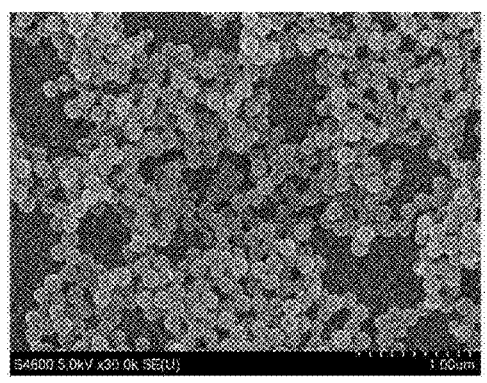
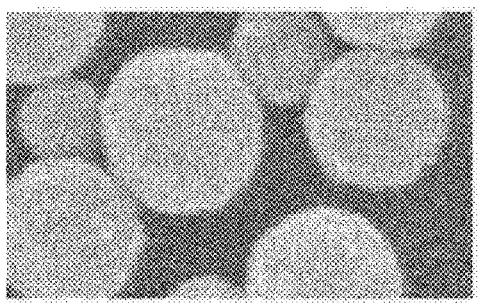 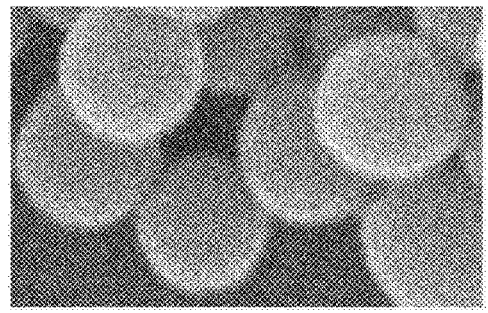

PHOSPHOR-INTEGRATED NANOPARTICLES USED IN FLUORESCENCE OBSERVATION

CROSS REFERENCE TO RELATED APPLICATIONS

This is the U.S. national stage of application No. PCT/JP2015/051522, filed Jan. 21, 2015; the entire contents of which is incorporated by reference.

TECHNICAL FIELD

The present invention relates to phosphor-integrated nanoparticles used in an immunofluorescent staining method.

BACKGROUND ART

With the recent expansion of molecular target drug therapy mainly based on antibody drugs, there is an increasing need for an accurate diagnostic method for more efficient use of molecular target drugs.

At present, a tissue collected from an affected part is dehydrated to be fixed and and is subjected to treatments such as paraffin blocking for fixation and subsequently cut into a section of 2 to 8 μm in thickness, after which paraffin is removed from the section (hereinafter, also referred to as "tissue section") and the section is subjected to staining of a target biological substance, followed by observation thereof under a microscope. In the thus obtained micrograph, a diagnosis is made on the basis of the morphological information and staining information, such as changes in the size and shape of cell nuclei and changes in the tissue pattern.

Conventionally, as tissue staining methods, hematoxylin-eosin [HE] staining using a dye and DAB staining using an enzyme have been widely employed; however, since the staining concentration in these methods is greatly affected by environmental conditions such as temperature and time, it is considered difficult to achieve an accurate quantitative measurement.

In recent years, immunostaining where a fluorescent dye and its aggregate are used as labeling reagents in place of a dye is performed and, particularly, by performing immunostaining in which a fluorescent dye is integrated, evaluations can be performed with such a high accuracy and quantitative performance that could not be achieved by a conventional enzyme method.

However, phosphor-integrated nanoparticles have a problem in that they yield largely variable test results depending on their quality.

For instance, when such phosphor-integrated nanoparticles are used for staining a pathological specimen, they are not always used immediately after the production and may be stored for a certain period until use. In that case, the phosphor-integrated nanoparticles are often stored in a state of being diluted in a storage medium such that the functions as a fluorescent label can be maintained.

However, after a long-term storage, the phosphor-integrated nanoparticles often precipitate and/or aggregate in the storage medium and, when the phosphor-integrated nanoparticles in such a state are directly used for immunostaining, coarse aggregates are generated in the resulting stained cellular tissue image, which may interfere with correctly counting the number of bright spots.

In order to avoid such a situation, conventionally, those phosphor-integrated nanoparticles that have been stored in a state of being diluted with a storage medium over a long time are required to be subjected to pretreatments such as solvent substitution, which is performed by repeating appropriate times the operations of centrifugation, supernatant removal, dilution with a staining solvent and redispersion by ultrasonication, and subsequent filtering treatment, prior to being used for staining; therefore, there is a problem of having to perform complicated operations.

For the quality control of phosphor-integrated nanoparticles, the shape and the surface microstructure of the particles are critical factors. Until now, it has been considered that higher sphericity and superior uniformity make phosphor-integrated nanoparticles more stable over a long period of time.

In Patent Document 1, it is described that, in the use of phosphor powder for the formation of a fluorescent film on the inner surface of a light-emitting surface of a light-emitting device (e.g., light-emitting surface of a CRT), a phosphor having a high average sphericity, specifically a sphericity of 0.95 or higher, allows the resulting film to exhibit excellent emission intensity and afterglow characteristics. However, Patent Document 1 offers neither description nor suggestion that a phosphor having a sphericity of less than 0.95 is a useful invention or that, particularly when such a phosphor is utilized as a labeling reagent or the like in tissue immunostaining, the phosphor exerts its actions and effects such as excellent dispersibility and excellent staining properties after long-term storage.

Further, an invention relating to the circumference ratio of nanoparticles is disclosed in Patent Document 2; however, this invention relates to particles used in a toner for electrostatic image development, and the technical significance of applying the properties associated with the circumference ratio in this invention to phosphor-integrated nanoparticles used for tissue immunostaining is neither obvious nor easily conceivable for those of ordinary skill in the art.

RELATED ART REFERENCES

Patent Documents

[Patent Document 1] JP 2002-194347A
[Patent Document 2] JP 2010-048932A

SUMMARY OF THE INVENTION

Problems to be Solved by the Invention

In order to solve the above-described problems, an object of the present invention is to provide phosphor-integrated nanoparticles whose precipitation and/or aggregation, particularly aggregation can be inhibited upon carrying out immunostaining therewith and which can thus be used for staining even after long-term storage without requiring a complicated operation, the phosphor-integrated nanoparticles preferably maintaining excellent performance, such as staining properties, even after long-term storage.

Technical Solution

The present inventors intensively studied to solve the above-described problems and came to focus on the sphericity and circumference ratio of phosphor-integrated nanoparticles as parameters that represent the state of the particle surface. As a result of further studies, the present inventors discovered that, by using phosphor-integrated nanoparticles having an average sphericity (f) of 0.80 to 0.95 and preferably an average circumference ratio of 0.50 to 0.95, precipitation and/or aggregation of the phosphor-integrated nanoparticles can be inhibited and, preferably, a staining liquid thereof is made unlikely to show deteriorated staining properties even after a relatively long-term storage period of, for example, about three months, thereby completing the present invention.

That is, the present invention provides the following phosphor-integrated nanoparticles and immunostaining solution.

[1] Phosphor-integrated nanoparticles having an average value of the sphericity (f) represented by the following Formula (1) of 0.80 to 0.95:

$$f=[M/(\pi/4)]^{0.5}/N\text{max} \tag{1}$$

(wherein, M represents the area of a projected cross-section (nm$^2$) of a fine particle, and Nmax represents the maximum diameter (nm) of the cross-section).

[2] The phosphor-integrated nanoparticles according to [1], which have an average value of the circumference ratio (R) represented by the following Formula (2) of 0.50 to 0.95:

$$R=2\pi([M/\pi]^{0.5})/r1 \tag{2}$$

(wherein, M represents the area of a projected cross-section (nm$^2$) of a fine particle, and r1 represents the circumferential length (nm) of the cross-section).

[3] The phosphor-integrated nanoparticles according to [1] or [2], wherein the matrix of the particles comprises an organic compound.

[4] The phosphor-integrated nanoparticles according to any one of [1] to [3], wherein the organic compound is a thermosetting resin.

[5] The phosphor-integrated nanoparticles according to any one of [1] to [4], which have an average particle size of 300 nm or smaller.

[6] The phosphor-integrated nanoparticles according to any one of [1] to [5], wherein a biological component-binding molecule is bound to the surfaces of the particles.

[7] An immunofluorescent staining solution comprising the phosphor-integrated nanoparticles according to [6].

Advantageous Effects of the Invention

By using the phosphor-integrated nanoparticles of the present invention in immunofluorescent staining, the dispersion of the phosphor-integrated nanoparticles is improved and precipitation and/or aggregation of the phosphor-integrated nanoparticles can be inhibited, so that a clear stained image can be preferably obtained even after a staining liquid of the nanoparticles is stored for a long time.

BRIEF DESCRIPTION OF THE DRAWINGS

FIG. 1 shows SEM images of the particles used in Example 1 and Comparative Example. From the enlarged images, it is seen that the particles of Example 1 have more prominent irregularities than the particles of Comparative Example 1.

MODE FOR CARRYING OUT THE INVENTION

Embodiments of the present invention will now be described; however, the present invention is not restricted thereto.

<Phosphor-integrated Nanoparticles>

The phosphor-integrated nanoparticles in the present invention are nano-sized particles having a structure in which a particle made of an organic or inorganic compound is used as a matrix and plural fluorescent substances (e.g., fluorescent dyes) are encapsulated therein and/or adsorbed on the surface thereof. The term "fluorescent substance" used herein refers to a substance whose electrons are excited when the substance is irradiated with an electromagnetic wave of a prescribed wavelength (X-ray, UV radiation or visible light) and absorbs the energy thereof and which releases an excess energy in the form of an electromagnetic wave during the transition from an excited state to the ground state, that is, a substance which emits "fluorescence", and the substance can be directly or indirectly bound to a secondary antibody. Further, the term "fluorescence" has a broad meaning and encompasses phosphorescence that has a long emission lifetime sustaining the emission even after the irradiation with an electromagnetic wave for excitation is terminated, as well as fluorescence in a narrow sense that has a short emission lifetime.

The phosphor-integrated nanoparticles of the present invention are particles characterized by at least their sphericity, wherein the average value of the sphericity (f) represented by the following formula defined as (1) is 0.80 to 0.95, preferably 0.90 to 0.95:

$$f=[M/(\pi/4)]^{0.5}/N\text{max} \tag{1}$$

(wherein, according to the formula of the sphericity (f) described in JP 2008-127279A, M represents the area of a projected cross-section (nm$^2$) of a fine particle, and Nmax represents the maximum diameter (nm) of the cross-section).

The formula of the sphericity (f) described in Patent Document 1, $f=4\pi A/L^2$ (wherein, A represents the actual area of a projected image, and L represents the circumferential length of each particle on the projected image), is converted into the Formula (1), and there is no substantial difference in definition between these formulae.

The sphericity is naturally required to be determined in three dimensions; however, since such determination is difficult due to the excessively small size of the particles and the sphericity thus has to be evaluated on a two-dimensional image in reality, the sphericity can be determined by the taking a large number of photographs under different photographing scenes and calculating the average of the measured values. In the present invention, the sphericity of phosphor-integrated nanoparticles is defined as a value obtained by taking an electron micrograph under an electron microscope (SEM), measuring the cross-sectional area and the maximum diameter for a sufficient number of particles and then taking an arithmetic mean of the values calculated by the above-described formula. The number of particles to be photographed under an SEM is preferably not less than 20, more preferably not less than 100.

Further, in the phosphor-integrated nanoparticles of the present invention, the average value of the circumference ratio (R) represented by the following Formula (2) (which represents the surface roughness) is preferably 0.50 to 0.95, more preferably 0.8 to 0.95:

$$R=2\pi([M/\pi]^{0.5})/r1 \tag{2}$$

(wherein, M represents the area of a projected cross-section (nm$^2$) of a fine particle, and r1 represents the circumferential length (nm) of the cross-section).

In the same manner as the sphericity, the circumference ratio is also defined as a value obtained by taking an electron micrograph under an electron microscope (SEM), measuring the cross-sectional area and the maximum diameter for a sufficient number of particles (preferably not less than 20 particles, more preferably not less than 100 particles), calculating the circumference ratio of each particle using the above-described formula and then taking an arithmetic mean of the calculated values.

Examples of the organic compound contained in the matrix of the particles include resins that are generally classified into thermosetting resins, such as melamine resins, urea resins, aniline resins, guanamine resin, phenol resins, xylene resins and furan resins; resins that are generally classified into thermoplastic resins, such as styrene resins, acrylic resins, acrylonitrile resins, AS resins (acrylonitrile-styrene copolymers) and ASA resins (acrylonitrile-styrene-methyl acrylate copolymers); other resins such as (co) polymers containing a structural unit formed by at least one selected from styrene, alkyl methacrylates, acrylonitrile and derivatives thereof, or polylactic acids; and polysaccharides, and examples of the inorganic compound include silica and glass. The matrix may be an organic compound or an inorganic compound; however, from the standpoint of the preservation of the staining properties, particles whose matrix is composed of an organic compound are more preferred, and particles composed of a thermosetting resin are still more preferred.

The above-described styrene, alkyl methacrylates, acrylonitrile and derivatives thereof are each a monofunctional or polyfunctional monomer which comprises, in a single molecule thereof, at least one vinyl group (C=C bond) involved in polymerization. Examples of the alkyl methacrylates include methyl methacrylate and ethyl methacrylate. The (co)polymers containing a structural unit formed by at least one selected from styrene, alkyl methacrylates, acrylonitrile and derivatives thereof comprise a structural unit formed by at least one of these monomers, and at least some of the hydrogens contained in the structural unit are substituted with charged substituents.

The molecular structure of the thermosetting resin is a three-dimensional network structure which is formed by polymers cross-linking with each other. Thus, a fluorescent substance encapsulated in the particles of the thermosetting resin is unlikely to elute out of the resin particles, so that an effect of inhibiting the occurrence of blur bright spots in fluorescence observation is attained.

Further, when the thermosetting resin has a positively charged or negatively charged substituent and the fluorescent substance constituting the phosphor-integrated nanoparticles of the present invention has a substituent with an electric charge opposite to that of the resin, since the fluorescent substance encapsulated in the resin particles are firmly integrated into the resin particles and this further makes dye elution unlikely to occur, the bleeding of the fluorescent dye in fluorescence observation performed after tissue staining can be inhibited, and the brightness of the stained image can thereby be ensured.

When the fluorescent substance is rhodamine, BODIPY, squarylium or an aromatic hydrocarbon-based dye molecule, the dye substance and the resin are strongly bound with each other by the interaction between the fluorescent substance and a hydrophobic moiety of the resin as well as the ionic bond formed by the substituents, which is more preferred because it enables to further strengthen the integration of the fluorescent substance in the resin particles.

The same effect can also be exerted when the thermosetting resin and the fluorescent substance are covalently bound with each other through any one of an amide bond, an ester bond, an ether bond and a C—N bond.

Among the above-exemplified thermosetting resins, a melamine resin can be particularly preferably used since it shows emission wavelength shift.

It is preferred that the above-described particles have an average size of 300 nm or smaller. Particularly, when the average size of the particles is larger than 300 nm, the staining properties are markedly deteriorated after storage.

In an embodiment where the above-described particles are utilized for detecting a biological substance of interest in the field of biology, it is preferred that a biological component-binding molecule be bound to the surfaces of the particles. The biological component-binding molecule is a molecule that is capable of specifically binding to a prescribed biological component so that a complex in which a phosphor-integrated nanoparticle and the biological substance of interest are directly or indirectly linked with each other can be formed. Examples of such a biological component-binding molecule include, but not limited to, antibodies, biotin, avidin (including streptavidin and NeutrAvidin), nucleic acids (including DNAs, RNAs, siRNAs, miRNAs and the like), sugar chains, and lectins. The bond may be a direct or indirect bond and, in order to improve the fluorescent labeling efficiency and to thereby minimizes the lapse of time that leads to degradation of fluorescence, it is preferred to use a complex in which a primary antibody and a phosphor-integrated nanoparticle are linked indirectly, namely through a non-covalent bond formed by utilizing antigen-antibody reaction, avidin-biotin reaction or the like.

One example of the immunostaining agent in which a probe and phosphor-integrated nanoparticles are linked indirectly is a complex of [primary antibody for the biological substance of interest] . . . [antibody (secondary antibody) for the primary antibody]-[fluorescent nanoparticle (phosphor-integrated particle)], wherein " . . . " represents a bond formed by an antigen-antibody reaction. The mode of the bond represented by "-" is not particularly restricted, and examples thereof include a covalent bond, an ionic bond, a hydrogen bond, a coordinate bond, physical adsorption, and chemical adsorption. As required, the bond may be formed via a linker molecule and, for example, a silane coupling agent which is a compound widely used for binding an inorganic substance with an organic substance can be employed. This silane coupling agent is a compound which has an alkoxysilyl group yielding a silanol group on hydrolysis at one end of the molecule and a functional group, such as a carboxyl group, an amino group, an epoxy group or an aldehyde group, at the other end, and binds with an inorganic substance via the oxygen atom of the silanol group. Specific examples of the silane coupling agent include mercaptopropyltriethoxysilane, glycidoxypropyltriethoxysilane, aminopropyltriethoxysilane, and polyethylene glycol chain-containing silane coupling agents (e.g., PEG-silane no. SIM6492.7, manufactured by Gelest, Inc.). These silane coupling agents may be used in a combination of two or more thereof.

The reaction between the phosphor-integrated nanoparticles and the silane coupling agent can be carried out by a known method. For example, the resulting fluorescent substance-containing silica nanoparticles are dispersed in pure water, and aminopropyltriethoxysilane is subsequently added thereto and allowed to react at room temperature for 12 hours. After the completion of the reaction, fluorescent substance-containing silica nanoparticles whose surfaces have been modified with aminopropyl groups can be obtained through centrifugation or filtration. Subsequently, by allowing amino groups to react with a carboxyl group of an antibody, the antibody can be bound to the fluorescent substance-containing silica nanoparticles through amide bonds. As required, a condensation agent such as EDC [1-ethyl-3-[3-dimethylaminopropyl]carbodiimide hydrochloride, manufactured by Pierce] can also be used.

As required, a linker compound which has a site capable of directly binding to an organic molecule-modified fluorescent substance-containing silica nanoparticle and a site capable of binding to a molecular target substance can be used. For example, when sulfo-SMCC [sulfosuccinimidyl-4-[N-maleimidomethyl]cyclohexane-1-carboxylate, manufactured by Pierce] which has both a site that selectively reacts with an amino group and a site that selectively reacts with a mercapto group is used, the amino groups of the fluorescent substance-containing silica nanoparticles modified with aminopropyltriethoxysilane and the mercapto group of the antibody are bound with each other, whereby fluorescent substance-containing silica nanoparticles bound with the antibody can be obtained.

For binding of a biological substance-recognizing site to fluorescent substance-containing polystyrene nanoparticles, the same procedure can be applied regardless of whether the fluorescent substance is a fluorescent dye or a semiconductor nanoparticle. That is, by impregnating polystyrene nanoparticles having a functional group, such as an amino group, with semiconductor nanoparticles or an organic fluorescent dye, phosphor-integrated polystyrene nanoparticles having the functional group can be obtained and, by using EDC or sulfo-SMCC in the subsequent process, phosphor-integrated polystyrene nanoparticles bound with an antibody can be prepared.

Another example of the immunostaining agent in which a probe and a phosphor are linked indirectly is a complex composed of three molecules that are linked together by a mode of [primary antibody for the biological substance of interest] . . . [antibody (secondary antibody) for the primary antibody]-[biotin]/[avidin]-[phosphor (fluorescent nanoparticle)] (wherein, " . . . " represents a bond formed by an antigen-antibody reaction; "-" represents a covalent bond which may be formed via a linker molecule as required; and "/" represents a bond formed by an avidin-biotin reaction).

A secondary antibody-biotin conjugate (biotin-modified secondary antibody) can be prepared using, for example, a commercially available biotin labeling reagent (kit) based on a known method by which biotin can be bound to a desired antibody (protein). Alternatively, if a biotin-modified secondary antibody in which biotin has been bound to a desired antibody in advance is commercially available, such a secondary antibody may be utilized as well.

A phosphor-integrated nanoparticle-avidin conjugate (avidin-modified phosphor) can also be prepared using, for example, a commercially available avidin labeling reagent (kit) based on a known method by which avidin can be bound to a phosphor. In this case, avidin may be of a modified type, such as streptavidin or NeutrAvidin, which exhibits a higher binding strength with biotin than avidin.

Specific examples of a method of preparing a phosphor-avidin conjugate include the followings. When the phosphor-integrated nanoparticles contain a resin as the matrix, a functional group of the resin and a functional group of avidin (protein) can be bound with each other through, as required, a linker molecule such as PEG that has functional groups at both ends of the molecule. For example, when the resin is a melamine resin, its functional group such as an amino group can be utilized and, when the resin is an acrylic resin, a styrene resin or the like, a monomer having a functional group (e.g., an epoxy group) in the side chain may be copolymerized with the resin to utilize the functional group itself or a functional group converted therefrom (e.g., an amino group generated by a reaction with aqueous ammonia), or these functional groups may be utilized to introduce other functional group(s). Further, when the phosphor-integrated nanoparticles are phosphor-integrated nanoparticles or inorganic semiconductor nanoparticles that contain silica as the matrix, a desired functional group can be introduced by surface modification with a silane coupling agent and, for example, an amino group can be introduced by using aminopropyltrimethoxysilane. Meanwhile, with regard to avidin, a thiol group can be introduced to avidin by allowing the amino group of avidin to react with, for example, N-succinimidyl-S-acetylthioacetate (SATA). Further, an amino group-containing phosphor and the thiol-introduced avidin can be linked with each other by utilizing a cross-linker reagent which has N-hydroxysuccinimide (NHS) ester that is reactive with an amino group and a maleimide group that is reactive with a thiol group on the respective ends of a polyethylene glycol (PEG) chain.

A secondary antibody-fluorescent dye conjugate (fluorescently labeled secondary antibody) can be prepared using, for example, a commercially available fluorescent labeling reagent (kit) based on a known method by which a desired fluorescent dye can be bound to a desired antibody (protein). Alternatively, if a fluorescently labeled secondary antibody in which desired fluorescent nanoparticles have been bound to a desired antibody in advance is commercially available, such a secondary antibody may be utilized as well.

The fluorescent substance to be integrated into the matrix is not particularly restricted.

(i) [Inorganic Phosphor]

Examples of an inorganic phosphor that can be used as the phosphor include quantum dots containing a Group II-VI compound, a Group III-V compound or a Group IV element as a component (hereinafter, such quantum dots are also referred to as "Group II-VI quantum dot", "Group III-V quantum dot" and "Group IV quantum dot", respectively). These quantum dots may be used individually, or a plurality thereof may be used in combination. These quantum dots may also be commercially available ones. Specific examples thereof include, but not limited to, CdSe, CdS, CdTe, ZnSe, ZnS, ZnTe, InP, InN, InAs, InGaP, GaP, GaAs, Si and Ge.

Quantum dots in which any of the above-described quantum dots is used as a core and a shell is provided thereon can also be used. Hereinafter, as a method of describing quantum dots having a shell, a quantum dot whose core is CdSe and shell is ZnS is indicated as "CdSe/ZnS". For example, CdSe/ZnS, CdS/ZnS, InP/ZnS, InGaP/ZnS, Si/SiO$_2$, Si/ZnS, Ge/GeO$_2$ and Ge/ZnS can be used; however, the quantum dot is not restricted thereto.

If necessary, a quantum dot whose surface has been treated with an organic polymer or the like may be used as well. Examples thereof include CdSe/ZnS having surface carboxy groups (manufactured by Invitrogen Corp.) and CdSe/ZnS having surface amino groups (manufactured by Invitrogen Corp.).

(ii) [Organic Phosphor]

Examples of an organic phosphor that can be used as the phosphor include substances known as organic fluorescent dyes, such as fluorescein-based dye molecules, rhodamine-based dye molecules, squarylium-based dye molecules, aromatic ring-containing dye molecules, carbopyronine-based dye molecules, pyrromethene-based dye molecules, Alexa Fluor (registered trademark, manufactured by Invitrogen)-based dye molecules, BODIPY (registered trademark, manufactured by Invitrogen)-based dye molecules, Cascade (registered trademark, manufactured by Invitrogen)-based dye molecules, Cy (registered trademark, manufactured by GE Healthcare)-based dye molecules, DY (registered trademark, manufactured by Dyomics GmbH)-based dye molecules, HiLyte (registered trademark, manufactured by AnaSpec Inc.)-based dye molecules, DyLight (registered trademark, manufactured by Thermo Fisher Scientific K.K.)-based dye molecules, ATTO (registered trademark, manufactured by ATTO-TEC GmbH)-based dye molecules, MFP (registered trademark, manufactured by Mobitec Co., Ltd.)-based dye molecules, coumarin-based dye molecules, NBD (registered trademark)-based dye molecules, pyrene-based dye molecules, Texas Red (registered trademark, manufactured by Life Technologies Corporation)-based dye molecules, cyanine-based dye molecules, perylene-based dye molecules and oxazine-based dye molecules.

Specific examples thereof include 5-carboxy-fluorescein, 6-carboxy-fluorescein, 5,6-dicarboxy-fluorescein, 6-carboxy-2',4,4',5',7,7'-hexachlorofluorescein, 6-carboxy-2',4,7,7'-tetrachlorofluorescein, 6-carboxy-4',5'-dichloro-2',7'-dimethoxyfluorescein, naphthofluorescein, 5-carboxy-rhodamine, 6-carboxy-rhodamine, 5,6-dicarboxy-rhodamine, rhodamine 6G; tetramethylrhodamine, X-rhodamine, Alexa Fluor 350, Alexa Fluor 405, Alexa Fluor 430, Alexa Fluor 488, Alexa Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 635, Alexa Fluor 647, Alexa Fluor 660, Alexa Fluor 680, Alexa Fluor 700, Alexa Fluor 750, BODIPY FL, BODIPY TMR, BODIPY 493/503, BODIPY 530/550, BODIPY 558/568, BODIPY 564/570, BODIPY 576/589, BODIPY 581/591, BODIPY 630/650, BODIPY 650/665 (all of which are manufactured by Invitrogen), methoxycoumarin, eosin, NBD, pyrene, Cy5, Cy5.5 and Cy7. These organic phosphors may be used individually, or a plurality thereof may be used in combination. The generic names of these dye molecules are assigned based on the main structure (skeleton) or registered trademark of the respective compounds; therefore, those of ordinary skill in the art should be able to properly understand the scope of fluorescent dyes belonging to the respective generic names without having to bear undue trial and error.

Examples of the fluorescent substance to be integrated into the phosphor-integrated nanoparticles include, in addition to the above-described semiconductor nanoparticles and fluorescent dyes, "long-afterglow phosphors" that comprise $Y_2O_3$, $Zn_2SiO_4$ or the like as a matrix and $Mn^{2+}$, $Eu^{3+}$ or the like as an activator.

Phosphor-integrated nanoparticles can be produced in accordance with a known method (see, for example, JP 2013-57937 A). More specifically, for example, fluorescent substance-integrated silica particles in which silica is used as a matrix and a fluorescent substance is encapsulated therein can be produced by adding dropwise a solution, in which inorganic semiconductor nanoparticles, a fluorescent substance such as an organic fluorescent dye and a silica precursor such as tetraethoxysilane are dissolved, to a solution in which ethanol and ammonia are dissolved, and subsequently hydrolyzing the silica precursor. Meanwhile, fluorescent substance-integrated resin particles in which a resin is used as a matrix and a fluorescent substance is adsorbed on the surfaces of the resin particles or encapsulated in the resin particles can be produced by preparing in advance a solution of the resin or a dispersion of fine particles of the resin, adding thereto inorganic semiconductor nanoparticles and a fluorescent substance such as an organic fluorescent dye, and subsequently stirring the resultant. Alternatively, fluorescent substance-integrated resin particles can also be produced by adding a fluorescent dye to a solution of a resin material and then allowing polymerization reaction to proceed. For example, in cases where a thermosetting resin such as a melamine resin is used as a matrix resin, organic phosphor-integrated nanoparticles can be produced by heating a reaction mixture, which contains a raw material of the resin (a monomer, an oligomer or a prepolymer, such as methylolmelamine obtained by condensation of melamine and formaldehyde), an organic fluorescent dye, and preferably further a surfactant and a polymerization reaction accelerator (e.g. an acid), and thereby allowing polymerization reaction to proceed by an emulsion polymerization method. Further, in cases where a thermoplastic resin such as a styrene-based copolymer is used as a matrix resin, organic phosphor-integrated nanoparticles can be produced by heating a reaction mixture, which contains a raw material of the resin, an organic fluorescent dye (as a resin material monomer, a monomer bound with an organic fluorescent dye through a covalent bond or the like in advance may be used as well) and a polymerization initiator (e.g. benzoyl peroxide or azobis-isobutyronitrile), and thereby allowing polymerization reaction to proceed by a radical polymerization method or an ionic polymerization method.

The phosphor-integrated nanoparticles of the present invention can be produced by adjusting the production conditions.

<Staining Solution>

In the present invention, an immunofluorescent staining solution obtained by diluting an immunostaining reagent for a biological substance of interest with a fluorescent nanoparticle diluent is also prescribed. The selection and dilution factor of the immunostaining reagent can be optimized in accordance with the affinity between the biological substance of interest and the immunostaining reagent.

<Biological Substance of Interest>

In the present invention, the biological substance of interest is a biological substance, particularly a protein (antigen) that is expressed on a tissue section, and refers to a subject of immunostaining performed with a fluorescent label for the purpose of quantification or detection mainly from the standpoint of pathological diagnosis.

The biological substance of interest is not particularly restricted and may be selected taking into consideration the use of the quantification method of the present invention, such as pathological diagnosis. Examples of a typical biological substance of interest include biological substances that are expressed on the cell membranes of various cancer tissues and can be utilized as biomarkers, such as growth factor receptors (e.g., EGFR (HER1) (Epidermal Growth Factor Receptor), HER2 (Human Epidermal Growth Factor Receptor), HER3, HER4, VEGFR (Vascular Endothelial Growth Factor Receptor), IGFR (Insulin-like Growth Factor Receptor), and HGFR (Hepatocyte Growth Factor Receptor)), and proteins serving as immune system receptors (e.g., PD-1 (Programmed cell death 1)). Examples of EGFR/HER include EGFR/HER1 (also called "ErbB1") which is overexpressed in cancer tissues such as colon cancer, EGFR2/HER2 (also called "ErbB2" or "neu") which is overexpressed in cancer tissues such as breast cancer, EGFR3/HER3, and EGFR4/HER4. Examples of VEGFR include VEGFR-1 (also called "Flt-1") and VEGFR-2 (also called "Flt-2" or "KDR"), which show enhanced expression in vascular endothelial cells of cancer tissues such as liver cancer and esophageal cancer, and VEGFR-3 (also called "Flt-4") which shows enhanced expression in lymphatic endothelial cells. For example, HER2 is suitable as the biological substance of interest when the quantification method of the present invention is performed in pathological diagnosis relating to breast cancer.

<Antibody>

The antibodies used in the present invention are selected in accordance with the intended use and may each be any antibody as long as it is capable of specifically recognizing and binding to a specific biological substance (antigen). The term "antibody" means, for example, an antibody for an antigen (e.g., HER2) associated with a disease (e.g., malignant tumor) (primary antibody), or a secondary to n-order antibody which binds with the primary antibody through an antigen-antibody reaction. Either of these antibodies is subjected to a reduction treatment as described below. The term "antibody" is herein used with a meaning that includes arbitrary antibody fragments or derivatives, encompassing Fabs, Fab'2s, CDRs, humanized antibodies, polyfunctional antibodies, single-chain antibodies (ScFv) and the like.

The antibodies used in the present invention may all be polyclonal antibodies; however, from the standpoint of the stability of quantification, they are preferably monoclonal antibodies. The kind of the animal (immune animal) used for producing the antibodies is not particularly restricted, and the animal may be selected from mice, rats, guinea pigs, rabbits, goats, sheep and the like as in conventional cases.

<Antigen>

Examples of the antigen include proteins (e.g., polypeptides and oligopeptides) and amino acids (including modified amino acids), as well as complexes formed by a protein or amino acid with a saccharide (e.g., oligosaccharide, polysaccharide or sugar chain), lipid or modified molecule thereof. Specifically, the antigen is, for example, but not particularly restricted to, an antigen (e.g., a tumor marker, a signal transducer or a hormone) associated with a target disease of the pathological diagnosis. Examples of the "antigen" also include cancer-associated antigens, such as cancer growth regulators, metastasis regulators, growth regulator receptors and metastasis regulator receptors; inflammatory cytokines, such as TNF-α (Tumor Necrosis Factor α) and IL-6 (Interleukin-6) receptors; and virus-associated molecules such as RSV F protein.

In addition to the above, examples of the antigen also include HER2, TOP2A, HER3, EGFR, P53 and MET, which are proteins derived from cancer-related genes. Further, examples of proteins that can be the antigen and are known to be derived from various cancer-related genes include the followings. Examples of proteins that can be the antigen and are derived from tyrosine kinase-related genes include ALK, FLT3, AXL, FLT4 (VEGFR3), DDR1, FMS (CSF1R), DDR2, EGFR (ERBB1), HER4 (ERBB4), EML4-ALK, IGF1R, EPHA1, INSR, EPHA2, IRR (INSRR), EPHA3, KIT, EPHA4, LTK, EPHA5, MER (MERTK), EPHA6, MET, EPHA7, MUSK, EPHA8, NPM1-ALK, EPHB1, PDGFRα (PDGFRA), EPHB2, PDGFRβ (PDGFRB), EPHB3, RET, EPHB4, RON (MST1R), FGFR1, ROS (ROS1), FGFR2, TIE2 (TEK), FGFR3, TRKA (NTRK1), FGFR4, TRKB (NTRK2), FLT1 (VEGFR1), and TRKC (NTRK3). Examples of proteins that can be the antigen and are derived from breast cancer-related genes include ATM, BRCA1, BRCA2, BRCA3, CCND1, E-Cadherin, ERBB2, ETV6, FGFR1, HRAS, KRAS, NRAS, NTRK3, p53, and PTEN. Examples of proteins that can be the antigen and are derived from carcinoid tumor-related genes include BCL2, BRD4, CCND1, CDKN1A, CDKN2A, CTNNB1, HES1, MAP2, MEN1, NF1, NOTCH1, NUT, RAF, SDHD, and VEGFA. Examples of proteins that can be the antigen and are derived from colon cancer-related genes include APC, MSH6, AXIN2, MYH, BMPR1A, p53, DCC, PMS2, KRAS2 (or Ki-ras), PTEN, MLH1, SMAD4, MSH2, STK11, and MSH6. Examples of proteins that can be the antigen and are derived from lung cancer-related genes include ALK, PTEN, CCND1, RASSF1A, CDKN2A, RB1, EGFR, RET, EML4, ROS1, KRAS2, TP53, and MYC. Examples of proteins that can be the antigen and are derived from liver cancer-related genes include Axin1, MALAT1, b-catenin, p16 INK4A, c-ERBB-2, p53, CTNNB1, RB1, Cyclin D1, SMAD2, EGFR, SMAD4, IGFR2, TCF1, and KRAS. Examples of proteins that can be the antigen and are derived from renal cancer-related genes include Alpha, PRCC, ASPSCR1, PSF, CLTC, TFE3, p54nrb/NONO, and TFEB. Examples of proteins that can be the antigen and are derived from thyroid cancer-related genes include AKAP10, NTRK1, AKAP9, RET, BRAF, TFG ELE1, TPM3, H4/D10S170, and TPR. Examples of proteins that can be the antigen and are derived from ovarian cancer-related genes include AKT2, MDM2, BCL2, MYC, BRCA1, NCOA4, CDKN2A, p53, ERBB2, PIK3CA, GATA4, RB, HRAS, RET, KRAS, and RNASET2. Examples of proteins that can be the antigen and are derived from prostate cancer-related genes include AR, KLK3, BRCA2, MYC, CDKN1B, NKX3.1, EZH2, p53, GSTP1, and PTEN. Examples of proteins that can be the antigen and are derived from bone tumor-related genes include CDH11, COL12A1, CNBP, OMD, COL1A1, THRAP3, COL4A5, and USP6.

—Method of Staining Tissue Section—

One example of a staining method using phosphor-integrated nanoparticles having a biological component-binding molecule bound on the surface, which is one mode of the present invention, will now be described. The method of preparing a tissue section (the term "tissue section" may be hereinafter simply referred to as "section" and used as a term that encompasses such sections as pathological sections) to which this staining method can be applied is not particularly restricted, and a tissue section prepared by a known procedure can be used.

(1. Sample Preparation Step)

(1-1. Deparaffinization Treatment)

The subject section is immersed in xylene contained in a vessel to remove paraffin. The temperature of this process is not particularly restricted and may be room temperature. The immersion time is preferably 3 minutes or longer but not longer than 30 minutes. If necessary, xylene may be replaced anew during the immersion.

Then, the section is immersed in ethanol contained in a vessel to remove xylene. The temperature of this process is not particularly restricted and may be room temperature. The immersion time is preferably 3 minutes or longer but not longer than 30 minutes. If necessary, ethanol may be replaced anew during the immersion.

The section is further immersed in water contained in a vessel to remove ethanol. The temperature of this process is not particularly restricted and may be room temperature. The immersion time is preferably 3 minutes or longer but not longer than 30 minutes. If necessary, water may be replaced anew during the immersion.

(1-2. Retrieval Treatment)

In accordance with a known method, a biological substance of interest to be stained is retrieved. The retrieval conditions are not particularly defined here; however, as a retrieval liquid, for example, 0.01 M citrate buffer (pH 6.0), 1 mM EDTA solution (pH 8.0), 5% urea or 0.1 M Tris-HCl buffer can be used. As a heating equipment, for example, an autoclave, a microwave oven, a pressure cooker or a water bath can be used. The temperature is not particularly restricted, and the retrieval may be performed at room temperature. The heating can be performed at a temperature of 50 to 130° C. for a period of 5 to 30 minutes.

Then, the thus retrieved section is immersed and washed in PBS contained in a vessel. The temperature of this process is not particularly restricted and may be room temperature. The immersion time is preferably 3 minutes or longer but not longer than 30 minutes. If necessary, PBS may be replaced anew during the immersion.

(2. Immunostaining Step)

In the immunostaining step, in order to stain the biological substance of interest, fluorescent nanoparticles having a site capable of directly or indirectly binding to the biological substance of interest are dispersed in the fluorescent nanoparticle diluent of the present invention, and the resulting dispersion is place on the section to allow the fluorescent nanoparticles to react with the biological substance of interest. The immunofluorescent staining solution used in the immunostaining step and the fluorescent nanoparticle diluent and other components used for the preparation thereof are as described above, and the immunofluorescent staining solution can be prepared in advance before the present step.

For example, when the immunostaining agent is a complex of [primary antibody (probe)] . . . [secondary antibody]-[biotin]/[avidin]-[fluorescent dye-containing nanoparticle (phosphor)] (wherein, " . . . " represents a bond formed by an antigen-antibody reaction; "-" represents a covalent bond which may be formed via a linker molecule as required; and "/" represents a bond formed by an avidin-biotin reaction), the processes of first immersing the pathological specimen in a primary antibody solution (primary reaction treatment), subsequently immersing the pathological specimen in a secondary antibody-biotin conjugate solution (secondary reaction treatment), and lastly immersing the pathological specimen in the staining solution for fluorescent nanoparticles according to the present invention in which avidin-fluorescent dye-containing nanoparticles are dispersed (fluorescent labeling treatment) may be performed.

The conditions for performing the immunostaining step, such as the temperature and time of the immersion of the pathological specimen in a prescribed solution (reagent) in each of the primary and secondary reaction treatments and the fluorescent labeling treatment, can be adjusted as appropriate in accordance with a conventional immunostaining method such that appropriate signals can be obtained.

The temperature of the immunostaining step is not particularly restricted, and the immunostaining step can be performed at room temperature. The reaction time is preferably 30 minutes or longer but not longer than 24 hours.

Prior to the above-described primary reaction treatment, it is preferred to add drops of a known blocking agent such as BSA-containing PBS or a surfactant such as Tween 20.

(3. Sample Post-Treatment Step)

After the completion of the immunostaining step, the pathological specimen is preferably subjected to treatments, such as fixation-dehydration, clearing and mounting, such that the tissue section is made suitable for observation.

The fixation-dehydration treatment can be performed by immersing the pathological specimen in a fixation liquid (a cross-linking agent such as formalin, paraformaldehyde, glutaraldehyde, acetone, ethanol, or methanol). The clearing can be performed by immersing the thus fixed and dehydrated pathological specimen in a clearing liquid (e.g. xylene). The mounting treatment can be performed by immersing the thus cleared pathological specimen in a mounting medium. The conditions for performing these treatments, such as the temperature and time of immersing the pathological specimen in each prescribed treatment liquid, can be adjusted as appropriate in accordance with a conventional immunostaining method such that appropriate signals can be obtained.

(3'. Optional Step)

In the present invention, if necessary, a staining step for morphological observation can be incorporated so that the morphology of cells, tissues, organs and the like can be observed in a bright field. The staining step for morphological observation can be performed in accordance with a conventional method. For the morphological observation of a tissue sample, eosin staining which stains cytoplasm, interstitial tissues, various fibers, erythrocytes and keratinocytes in red to dark red is typically employed. Further, hematoxylin staining which stains cell nuclei, calcareous parts, cartilaginous tissues, bacteria and mucus in livid to light blue is also typically employed (a method of simultaneously performing these two staining processes is known as "hematoxylin-eosin staining" (HE staining)). In cases where the staining step for morphological observation is incorporated, it may be performed after or before the immunostaining step.

(4. Evaluation Step)

(4-1. Observation and Image-Capturing)

In the observation and image-capturing step, in the same visual field under a microscope at a desired magnification, the pathological specimen is irradiated with excitation lights corresponding to the respective phosphors with which the biological substance of interest is fluorescently labeled in the immunostaining step, and immunostained images produced by the fluorescence emitted from the phosphors are observed and captured. These excitation lights can be irradiated using, for example, a laser light source installed in a fluorescence microscope and, as required, an optical filter for excitation light which selectively transmits light of a prescribed wavelength. The immunostained images can be captured using, for example, a digital camera mounted on the fluorescence microscope. In the process of capturing the immunostained images, by using, as required, an optical filter for fluorescence which selectively transmits light of a prescribed wavelength, immunostained images including only the desired fluorescence, from which undesired fluorescence, noise-causing exciting light and other lights are excluded, can be obtained.

(4-2. Image Processing and Signal Measurement)

In the image processing and measurement step, on the immunostained images captured for the biological substance of interest, the fluorescently labeled signals corresponding to the biological substance of interest are measured based on the results of image processing, and the fluorescently labeled signals corresponding to the biological substance of interest that exist in the cell membrane region are identified.

The fluorescently labeled signals are preferably measured in terms of the number of fluorescent bright spots.

Examples of software that can be used for the image processing include "ImageJ" (open source). The use of such an image processing software enables to perform a process of extracting bright spots of a prescribed wavelength (color) from the immunostained images and determining the total brightness of the bright spots and a process of measuring the number of bright spots having a brightness of not less than a prescribed value, particularly those processes for carrying out the below-described first and second embodiments, in a semi-automatic and prompt manner.

In the present invention, by using first and second stained images, the fluorescently labeled signals corresponding to the biological substance of interest existing in the cell membrane region (that is, on the cell membranes) of the stained images can be specified and extracted simultaneously with the measurement of the fluorescently labeled signals. Particularly, in those cases where fluorescent dye-containing nanoparticles are used as the phosphor for the biological substance of interest and a fluorescent dye is used as the phosphor for a reference biological substance, examples of preferred embodiments include the following first and second embodiments.

EXAMPLES

The present invention will now be described in detail by way of examples thereof; however, the present invention is not restricted thereto.
—Synthesis Examples of Phosphor-Integrated Nanoparticles—
[Particle α-1 and α-2]
Perylene Diimide-Integrated Nanoparticles By treating N,N-bis(2,6-diisopropylphenyl)-1,6,7,12-tetraphenoxyperylene-3,4:9,10-tetracarboxdiimide with concentrated sulfuric acid, a sulfo group was introduced to obtain a corresponding sulfonic acid. This sulfonic acid was converted into a corresponding acid chloride by a conventional method. After adding 14.4 mg of the thus obtained acid chloride to 22.5 mL of water, the resultant was heated at 70° C. for 20 minutes on a hot stirrer and 0.65 g of a melamine resin NIKALAC MX-035 (manufactured by Nippon Carbide Industries Co., Ltd.) was added thereto, followed by heating of the resulting mixture with stirring for another 5 minutes. Then, 100 μL of formic acid was further added, and the resultant was heated with stirring at 60° C. for 20 minutes and subsequently cooled to room temperature. Thereafter, the resulting reaction mixture was placed in a centrifugal tube and centrifuged at 12,000 rpm for 20 minutes, followed by removal of the resulting supernatant. The precipitates were washed with ethanol and water.

Then, 0.1 mg of the thus obtained particles was dispersed in 1.5 mL of EtOH (ethanol), and 2 μL of aminopropyltrimethoxysilane LS-3150 (manufactured by Shin-Etsu Chemical Co., Ltd.) was added thereto. The resultant was allowed to react for 8 hours so as to perform a surface amination treatment.

The thus obtained perylene diimide-integrated nanoparticles were adjusted with PBS (phosphate-buffered physiological saline) containing 2 mM of EDTA (ethylenediamine tetraacetic acid) to a concentration of 3 nM, and this solution was mixed with SM(PEG)12 (manufactured by Thermo Fisher Scientific K.K.; succinimidyl-[(N-maleomidopropionamid)-dodecaethylene glycol]ester) to a final concentration of 10 mM and allowed to react for 1 hour. The thus obtained mixture was centrifuged at 10,000 G for 20 minutes and the resulting supernatant was removed, after which PBS containing 2 mM of EDTA was added to disperse the precipitates, and the resulting dispersion was centrifuged again. The precipitates were washed three times by the same procedure to obtain perylene diimide-integrated nanoparticles having a maleimide group at a terminal (particles α-1).

When the particle size was measured for the thus obtained particles α-1 under an electron microscope, the average particle size was found to be 150 nm. Further, particles α-2 having a particle size different from the particles α-1 were synthesized in the same manner as the particles α-1, except that the amount of the dye and that of the resin were reduced from 14.4 mg to 3.6 mg and from 0.65 mg to 0.21 mg, respectively.

Streptavidin-Modified Perylene Diimide-Integrated Nanoparticles

After allowing streptavidin (SA: manufactured by Wako Pure Chemical Industries, Ltd.) to react with an SH group-introducing reagent N-succinimidyl-S-acetylthioacetate (SATA), a thiol group was introduced to this streptavidin by performing a known hydroxylamine treatment for deprotection of S-acetyl group. Then, by filtering the resultant through a gel filtration column (Zeba Spin Desalting Columns, manufactured by Thermo Fisher Scientific K.K.: No. 89889), streptavidin capable of binding to the perylene diimide-integrated nanoparticles having a maleimide group at a terminal (particles α-1 and α-2) was obtained.

The thus obtained streptavidin solution was mixed with 1 mL of a phosphor-integrated nanoparticle-containing liquid obtained by diluting the above-described particles α-1 and α-2 with PBS containing 2 mM of EDTA to a concentration of 1 nM, and the resulting mixture was allowed to react at room temperature for 1 hour, whereby the particles α-1 and α-2 were bound with streptavidin.

The reaction was terminated with an addition of 10 mM mercaptoethanol. The resulting solution was then centrifuged and washed with PBS containing 2 mM of EDTA, and only streptavidin-modified particles, α-1-SA and α-2-SA, were recovered.
[Particles β-1, β-2, β-3 and β-4']
Texas Red-integrated Nanoparticles An organoalkoxysilane compound was obtained by mixing 3.4 mg of Texas Red dye and 3 μL of 3-aminopropyltrimetoxysilane (KBM903, manufactured by Shin-Etsu Chemical Co., Ltd.) in N,N-dimethylformamide (DMF).

Then, 0.6 mL of the thus obtained organoalkoxysilane compound was mixed with 48 mL of 99% ethanol, 0.6 mL of tetraethoxysilane (TEOS), 2 mL of ultrapure water and 2.0 mL of 28%-by-mass aqueous ammonia for 3 hours at 5° C.

The thus prepared mixture was centrifuged at 10,000 G for 20 minutes, and the resulting supernatant was removed. A washing process of dispersing the thus obtained precipitates by adding thereto ethanol and subsequently centrifuging again the resulting dispersion was repeated three times, whereby Texas Red-integrated nanoparticles were obtained.

The thus obtained phosphor-integrated nanoparticles were adjusted with PBS (phosphate-buffered physiological saline) containing 2 mM of EDTA (ethylenediamine tetraacetic acid) to a concentration of 3 nM, and this solution was mixed with SM(PEG)12 (manufactured by Thermo Fisher Scientific K.K.; succinimidyl-RN-maleomidopropionamid)-dodecaethylene glycollester) to a final concentration of 10 mM and allowed to react at 5° C. for 1 hour. The thus obtained mixture was centrifuged at 10,000 G for 20 minutes and the resulting supernatant was removed, after which PBS containing 2 mM of EDTA was added to disperse the precipitates, and the resulting dispersion was centrifuged again. The precipitates were washed three times by the same procedure to obtain Texas Red-integrated nanoparticles having a maleimide group at a terminal (β-1). When the particle size was measured for the thus obtained particles β-1 under an electron microscope, the average particle size was found to be 150 nm. Further, particles β-2 were synthesized in the same manner as the particles β-1 except that 28%-by-mass aqueous ammonia was changed to 14%-by-mass aqueous ammonia, and particles β-3 and β-4 were also synthesized in the same manner as the particles β-1 except that the amount of 28%-by-mass aqueous ammonia used in the synthesis was changed from 2.0 mL to 2.5 mL and 3.1 mL, respectively.

Streptavidin-Modified Texas Red-Integrated Nanoparticles

Streptavidin (manufactured by Wako Pure Chemical Industries, Ltd.) was added to a borate buffer and subsequently allowed to react with an SH group-introducing reagent (2-iminothiolane hydrochloride, manufactured by Sigma-Aldrich) at room temperature for 1 hour to introduce a thiol group to the streptavidin. Then, by filtering the thus obtained streptavidin solution through a gel filtration column (Zeba Spin Desalting Columns, manufactured by Thermo Fisher Scientific K.K.: No. 89889), streptavidin capable of binding to the Texas Red-integrated nanoparticles having a maleimide group at a terminal (particles β-1, β-2, β-3 and β-4) was obtained.

The thus obtained streptavidin was mixed with 740 μL of a liquid obtained by diluting the above-described particles with PBS containing 2 mM of EDTA to a concentration of 0.67 nM, and the resulting mixture was allowed to react at room temperature for 1 hour, whereby the particles β-1, β-2, β-3 and β-4 were bound with streptavidin.

The reaction was terminated with an addition of 10 mM mercaptoethanol. The resulting solution was then centrifuged and purified, and only streptavidin-modified particles, β-1-SA, β-2-SA, β-3-SA and β-4-SA, were recovered.

Antibody-Modified Texas Red-Integrated Nanoparticles

First, an antibody having a thiol group at a terminal was prepared as follows. Then, this antibody having a thiol group at a terminal was allowed to react with the above-described particles β-2 and β-3.

Reduction Step: Reduction Treatment (SH Group-Introducing Treatment) of Anti-HER2 Antibody An anti-HER2 antibody ("anti-HER2 rabbit monoclonal antibody (4B5)" manufactured by Ventana Medical Systems, Inc., molecular weight=148,000 g/mol) in an amount of 100 μg was dissolved in 100 μL, of PBS. Then, 10 μL of 1M mercaptoethanol was added to this antibody solution and allowed to react at room temperature for 30 minutes to reduce the antibody, after which the reaction solution was subjected to a gel filtration column to obtain a solution of SH group-containing anti-HER2 antibody.

The thus obtained SH group-containing anti-HER2 antibody and the particles β-2 and β-3 were mixed and allowed to react for 1 hour in PBS at room temperature. Then, the binding reaction was terminated with an addition of 4 μL of 10 mM 2-mercaptoethanol and the resulting solution was centrifuged at 10,000 G for 60 minutes, followed by removal of the resulting supernatant. Thereafter, PBS containing 2 mM of EDTA was added to disperse the precipitates, and the resulting dispersion was centrifuged again. The precipitates were washed three times by the same procedure. Lastly, the precipitates were dispersed in 500 μL of PBS to obtain silica nanoparticles bound with the anti-HER2 antibody (antibody-bound phosphor-integrated nanoparticles) β-2-Ab and β-3-Ab.

[Particles θ-1 and θ-2]

Perylene Diimide-Integrated Melamine Particles

After adding 2.5 mg of a perylene diimide sulfonic acid derivative to 22.5 mL of water, the resultant was heated at 70° C. for 20 minutes on a hot stirrer and 1.5 g of a water-soluble melamine resin "NIKALAC MX-035" (manufactured by Nippon Carbide Industries Co., Ltd.) was added thereto, followed by heating of the resulting mixture with stirring for another 5 minutes. Then, 100 μL of formic acid was further added, and the resultant was heated with stirring at 60° C. for 20 minutes and subsequently cooled to room temperature. Thereafter, the resulting reaction mixture was placed in a centrifugal tube and centrifuged at 12,000 rpm for 20 minutes, followed by removal of the resulting supernatant. The precipitates were washed with ethanol and water.

The thus obtained perylene diimide-integrated nanoparticles and SM(PEG)12 (manufactured by Thermo Fisher Scientific K.K.; succinimidyl-[(N-maleomidopropionamid)-dodecaethylene glycol]ester) were mixed and allowed to react for 1 hour. The thus obtained mixture was centrifuged at 10,000 G for 20 minutes and the resulting supernatant was removed, after which PBS containing 2 mM of EDTA was added to disperse the precipitates, and the resulting dispersion was centrifuged again. The precipitates were washed three times by the same procedure to obtain perylene diimide-integrated nanoparticles having a maleimide group at a terminal (particles θ-1).

When the particle size was measured for the thus obtained particles C under an electron microscope, the average particle size was found to be 150 nm. Further, particles θ-2 were also synthesized in the same manner as the particles θ-1, except that the amount of formic acid used in the synthesis was reduced from 100 μL to 50 μL.

Streptavidin-Modified Perylene Diimide-Integrated Melamine Particles

In the same manner as in the preparation of the streptavidin-modified Texas Red-integrated nanoparticles, streptavidin capable of binding to perylene diimide-integrated nanoparticles having a maleimide group at a terminal (particles θ-1 and θ-2) was obtained and allowed to react with the particles θ-1 and θ-2 and the resultant was centrifuged and then purified, whereby streptavidin-modified particles θ-1-SA and θ-2-SA were recovered.

Antibody-Modified Perylene Diimide-Integrated Melamine Particles

θ-2-Ab was prepared from θ-2 in the same manner as in the antibody modification method used for preparing β-2-Ab from β-2.

(Evaluation 1) Evaluation of Precipitation and Aggregation of Phosphor-Integrated Nanoparticles The results of evaluating precipitation and aggregation using the particles α-1 and α-2 in Examples 1 and 6, respectively; the particles β-1, β-2, β-3 and β-4 in Examples 2 to 5, respectively; FluoSpheres Carboxylate-Modified Microspheres, 0.2 μm, red fluorescent (580/605), 2% solids (F-8810, manufactured by Invitrogen Corp.: phosphor-integrated nanoparticles containing carboxylate-modified polystyrene as matrix) in Comparative Example 1; and the particles θ-1 and θ-2 in Comparative Examples 2 and 3, respectively, are shown below (Table 1).

Further, the results of evaluating precipitation and aggregation of the above-described particles after modification of their surfaces with a biological component-binding molecule are shown in Table 2.

The above-described types of phosphor-integrated nanoparticles and biological component-binding molecule-bound phosphor-integrated nanoparticles were each subjected to the evaluation of precipitation and aggregation after being stored in a refrigerator at 4° C. for one week in a state of being contained in a storage medium. As the storage medium, a Tris buffer (pH=6.9) containing 0.6% α-casein, 0.6% β-casein, 3% BSA, 0.1% TWEEN (registered trademark) 20 and 0.015N $NaN_3$ (pH=6.9) was employed.

The precipitation and aggregation of the particles were evaluated visually or using TURBISCAN (trademark) (TURBISCAN Lab) manufactured by Formulaction SA.

As for the measurement conditions in the case of using TURBISCAN (trademark), the backscatter intensity (transmitted light) was measured using a light source emitting an infrared radiation of 880 nm in wavelength for the media containing the respective phosphor-integrated nanoparticles or biological component-binding molecule-bound phosphor-integrated nanoparticles.

Then, with the backscatter intensity (transmitted light) measured at the center of the height in the initial observation being defined as "I'A" and the backscatter intensity (transmitted light) measured at the center of the height after one week of storage being defined as "I'B", the rate of change in the backscatter intensity (transmitted light) at the center of the height, D' (%), was calculated as follows.

$$D'=(I'B-I'A)/I'A\times100$$

Tables 1 and 2 show the rate of change (D') in precipitation and aggregation determined for the respective phosphor-integrated nanoparticles. A correlation that no aggregation is visually observed when the value measured by TURBISCAN is −1 or larger was confirmed.

(Evaluation 2) Evaluation of Retention of Staining Intensity in Use of Phosphor-Integrated Nanoparticles Next, in order to evaluate the storage performance, the following immunostaining, morphological staining and observation were performed using the respective biological component-binding molecule-bound phosphor-integrated nanoparticles described above which were put into the above-described storage medium immediately after the synthesis and had been stored in a refrigerator at 4° C. for 3 months.

(2-1) Sample Preparation Step

As a tissue cell slide, a breast cancer tissue array manufactured by US Biomax, Inc. (model: BR243 Series (24-core); core diameter 1.5 mm) was employed.

The tissue cell slide was deparaffinized in accordance with a conventional method and then washed by substitution with water. The thus washed tissue cell slide was subjected to a 5-minute autoclave treatment at 121° C. in 10 mM citrate buffer (pH 6.0), thereby performing an antigen retrieval treatment.

(2-2) Immunostaining Step

After the retrieval treatment, the tissue array slide was washed with PBS buffer and then subjected to a 1-hour blocking treatment with 1% BSA-containing PBS buffer in a moist chamber. After the blocking treatment, an anti-HER2 rabbit monoclonal antibody (4B5, manufactured by Ventana Medical Systems, Inc.) diluted with 1% BSA-containing PBS buffer to a concentration of 0.05 nM was allowed to react with the tissue cell slide for 2 hours. After washing this tissue cell slide with PBS buffer, the tissue cell slide was further allowed to react for 30 minutes with a biotin-labeled anti-rabbit monoclonal antibody that would bind to 4B5 and had been diluted with 1% BSA-containing PBS buffer to a concentration of 2 µg/mL.

After the reaction with the biotin-labeled anti-rabbit monoclonal antibody, the tissue cell slide was stained with the biological component-binding molecule-bound phosphor-integrated nanoparticles.

(2-3) Fluorescent Labeling Treatment of Immunostaining

It is noted here that, for staining with the biological component-binding molecule-bound phosphor-integrated nanoparticles immediately after the synthesis thereof, the tissue cell slide was allowed to react for 3 hours with the phosphor-integrated nanoparticles of immediately after the synthesis that had been diluted with 1% BSA-containing PBS buffer to a concentration of 0.2 nM, in a neutral pH environment (pH 6.9 to 7.4) at room temperature. Prior to the dilution of the biological component-binding molecule-bound phosphor-integrated nanoparticles to a concentration of 0.2 nM, the solvent was substituted with the above-described storage medium by repeating appropriate times the process of centrifugation, removal of supernatant, dilution with the storage medium and redispersion by ultrasonication, and the resultant was subsequently subjected to a filtration treatment (0.65 µm, manufactured by Merck Millipore Corporation).

Meanwhile, staining with the biological component-binding molecule-bound phosphor-integrated nanoparticles after three months of storage in the storage medium was also performed in the same manner, except that the phosphor-integrated nanoparticles that had been stored for three month in the storage medium were used in place of the phosphor-containing resin particles of immediately after the synthesis that were diluted to 0.2 nM. In this case, the phosphor-integrated nanoparticles, which had been stored in the form of the above-described storage medium containing the fluorescent dye-containing resin particles, were diluted with 1% BSA-containing PBS buffer to a concentration of 0.2 nM and then used for the staining. After the reaction with the phosphor-integrated nanoparticles, the tissue cell slide was washed with PBS buffer.

(2-4) Sample Post-treatment Step

The tissue cell slides subjected to the above-described immunostaining were each further subjected to morphological staining. Specifically, the immunostained tissue cell slide was subjected to hematoxylin staining (HE staining) for 1 minute using Mayer's hematoxylin solution. Then, the tissue cell slide was washed with 45° C. running water for 3 minutes. Next, an operation of immersing the tissue cell slide in pure ethanol for 5 minutes was repeated four times to perform washing and dehydration. Subsequently, an operation of immersing the tissue cell slide in xylene for 5 minutes was repeated four times to perform clearing. Lastly, the tissue section was mounted with a mounting medium ("Entellan New", manufactured by Merck KGaA) to give a sample slide for observation.

(2-5) Evaluation Step (2-5-1) Observation and Image-capturing Step

The tissue section on the sample slide that had been subjected to the above-described immunostaining and morphological staining was allowed to emit fluorescence by irradiating thereto a prescribed excitation light. The tissue section in this state was observed and photographed under a fluorescence microscope (BX-53, manufactured by Olympus Corporation). It is noted here that the observation and photographing were performed in 10 visual fields for each core (a single tissue spot) on the sample slide. In this process, an objective lens of ×40 magnification and an ocular lens of ×10 magnification were used.

(2-5-2) Image Processing and Measurement Step

Further, the bright spots were measured by ImageJ Find-Maxima method.

The excitation light was set to have a wavelength of 575 to 600 nm through an optical filter. In addition, the wavelength range (nm) of the fluorescence to be observed was also set at 612 to 682 nm through an optical filter.

The conditions of the excitation wavelength in the microscope observation and image acquisition were set such that the intensity of the irradiation light in the vicinity of the center of the visual field was 900 W/cm$^2$ for excitation at 580 nm. In the image acquisition process, a photograph was taken by arbitrarily setting the exposure time such that the image brightness was not saturated (for example, the exposure time was set at 4,000 µs).

The results of Evaluation 2 are shown in Table 2 below.

From the results shown in Tables 1 and 2, the phosphor-integrated nanoparticles having an average sphericity (f) of 0.80 to 0.95 and those particles bound with a biological component-binding molecule were evaluated to show neither precipitation nor aggregation after one week of storage; however, those particles having an average sphericity (f) outside this range were evaluated to cause precipitation and aggregation after the storage. The production method of the particles α-1 and that of the particles θ-1 are slightly different as described above, and the difference is considered to be reflected in the differences in parameter values such as sphericity. Further, there was hardly any change in the parameter values, such as sphericity, between before and after the binding with a biological component-binding molecule.

TABLE 1

Particles prior to being bound with biological component-binding molecule

| | Particle | Matrix | Fluorescent dye | Particle size | Sphericity (f) | Circumference ratio (R) | Precipitation and aggregation of phosphor-integrated nanoparticles (visual observation) | Aggregation of phosphor-integrated nanoparticles (TURBISCAN measurement) |
|---|---|---|---|---|---|---|---|---|
| Example 1 | α-1 | melamine | perylene diimide | 150 nm | 0.93 | 0.9 | absent | −0.1 |
| Example 2 | β-1 | silica | Texas Red | 150 nm | 0.93 | 0.88 | absent | −0.5 |
| Example 3 | β-2 | silica | Texas Red | 150 nm | 0.85 | 0.9 | absent | 0 |
| Example 4 | β-3 | silica | Texas Red | 280 nm | 0.93 | 0.88 | absent | −0.4 |
| Example 5 | β-4 | silica | Texas Red | 320 nm | 0.93 | 0.78 | absent | −0.7 |
| Example 6 | α-2 | melamine | perylene diimide | 40 nm | 0.93 | 0.9 | absent | −0.4 |
| Comparative Example 1 | Molecular Probes ® FluoSpheres beads | polystyrene | red dye | 170 nm | 0.99 | 0.98 | present | not performed |
| Comparative Example 2 | θ-1 | melamine | perylene diimide | 150 nm | 0.98 | 0.91 | present | −2.2 |
| Comparative Example 3 | θ-2 | melamine | perylene diimide | 150 nm | 0.74 | 0.62 | present | −3 |

TABLE 2

Particles bound with biological component-binding molecule

| | Particle | Matrix | Fluorescent dye | Particle modification | Particle size | Sphericity (f) | Circumference ratio (R) | Aggregation of biological component-binding molecule-bound phosphor-integrated nanoparticles (visual observation) | Aggregation of biological component-binding molecule-bound phosphor-integrated nanoparticles (TURBISCAN measurement) | Comparison of staining results of HER2-expressing cells between the use of biological component-binding molecule-bound particles prior to three-month storage and the use of biological component-binding molecule-bound particles after three-month storage |
|---|---|---|---|---|---|---|---|---|---|---|
| Example 7 | α-1-SA | melamine | perylene diimide | SA | 150 nm | 0.93 | 0.91 | absent | −0.3 | Number of bright spots: not reduced |
| Example 8 | β-1-SA | silica | Texas Red | SA | 150 nm | 0.93 | 0.88 | absent | −0.4 | Number of bright spots: reduced to ½ |
| Example 9 | β-2-SA | silica | Texas Red | SA | 150 nm | 0.88 | 0.9 | absent | 0 | Number of bright spots: reduced to ½ |
| Example 10 | β-2-Ab | silica | Texas Red | antibody | 150 nm | 0.85 | 0.92 | absent | −0.5 | not performed |
| Example 11 | β-3-SA | silica | Texas Red | SA | 280 nm | 0.91 | 0.87 | absent | −0.1 | Number of bright spots: reduced to ½ |
| Example 12 | β-3-Ab | silica | Texas Red | antibody | 280 nm | 0.93 | 0.88 | absent | −0.7 | not performed |
| Example 13 | β-4-SA | silica | Texas Red | SA | 320 nm | 0.93 | 0.72 | absent | −0.3 | Number of bright spots: reduced to 1/10 |
| Example 14 | α-2-SA | melamine | perylene diimide | SA | 40 nm | 0.93 | 0.91 | absent | −0.4 | Number of bright spots: not reduced |
| Comparative Example 4 | θ-1-SA | melamine | perylene diimide | SA | 150 nm | 0.97 | 0.91 | present | −1.9 | Number of bright spots: reduced to ½ |
| Comparative Example 5 | θ-2-SA | melamine | perylene diimide | SA | 150 nm | 0.77 | 0.62 | present | −1.9 | Number of bright spots: reduced to 1/10 |
| Comparative Example 6 | θ-2-Ab | melamine | perylene diimide | antibody | 150 nm | 0.75 | 0.62 | present | −2.8 | Number of bright spots: reduced to 1/10 |

The invention claimed is:

1. Tissue staining phosphor-integrated nanoparticles having an average value of the sphericity (f) represented by the following Formula (1) of 0.80 to 0.95 and an average value of the circumference ratio (R) represented by the following Formula (2) of 0.80 to 0.95:

$$f=[M/(\pi/4)]^{0.5}/N\text{max} \quad (1)$$

wherein, M represents the area of a projected cross-section (nm²) of a fine particle, and Nmax represents the maximum diameter (nm) of said cross-section, $$R=2\pi([M/\pi]^{0.5})/r1 \quad (2)$$

wherein, M represents the area of a projected cross-section (nm²) of a fine particle, and r1 represents the circumferential length (nm) of said cross-section,
wherein the phosphor-integrated nanoparticles comprise matrix particles comprising at least one of:
a) a resin selected from the group consisting of thermosetting resins, styrene resins, acrylic resins, acrylonitrile resins, acrylonitrile-styrene copolymers, acrylonitrile-styrene-methyl acrylate copolymers, other copolymers containing a structural unit comprising at least one monomer selected from the group consisting of styrene, an alkyl methacrylates, acrylonitrile, and derivatives thereof;
b) polylactic acids;
c) silica; or
d) glass.

2. The tissue staining phosphor-integrated nanoparticles according to claim 1, wherein the matrix of said particles comprises an organic compound.

3. The tissue staining phosphor-integrated nanoparticles according to claim 2, wherein said organic compound is a thermosetting resin.

4. The tissue staining phosphor-integrated nanoparticles according to claim 1, which have an average particle size of 300 nm or smaller.

5. The tissue staining phosphor-integrated nanoparticles according to claim 1, wherein a biological component-binding molecule is bound to the surfaces of said particles.

6. An immunofluorescent staining solution comprising the tissue staining phosphor-integrated nanoparticles according to claim 5.

7. The tissue staining phosphor-integrated nanoparticles according to claim 1, comprising particles comprising a matrix particle and a phosphor contained in the matrix particle.

8. Tissue staining phosphor-integrated nanoparticles according to claim 1, wherein the phosphor-integrated nanoparticles comprise matrix particles having a particle size of 300 nm or less.

9. Tissue staining phosphor-integrated nanoparticles according to claim 1, wherein the phosphor-integrated nanoparticles comprise matrix particles comprising at least one of a resin selected from the group consisting of polystyrene, a melamine resin, an urea resin, an aniline resin, a guanamine resin, a phenol resin, a xylene resin, and a furan resin.

10. Tissue staining phosphor-integrated nanoparticles according to claim 1, wherein the phosphor-integrated nanoparticles are not visually precipitated nor visually aggregated after storage for one week at 4° C.

11. Tissue staining phosphor-integrated nanoparticles according to claim 1, wherein the phosphor-integrated nanoparticles comprise matrix particles comprising at least one of:
a) a resin selected from the group consisting of thermosetting resins, styrene resins, acrylic resins, acrylonitrile resins, acrylonitrile-styrene copolymers, acrylonitrile-styrene-methyl acrylate copolymers, other copolymers containing a structural unit comprising at least one monomer selected from the group consisting of styrene, an alkyl methacrylate, acrylonitrile, and derivatives thereof;
b) polylactic acid; or
c) glass.

* * * * *